US010464887B2

(12) United States Patent
Hsu

(10) Patent No.: US 10,464,887 B2
(45) Date of Patent: Nov. 5, 2019

(54) METHOD FOR PRODUCING ACTIVE INGREDIENT FOR RIVASTIGMINE FREE BASE TRANSDERMAL PATCH AND RIVASTIGMINE FREE BASE TRANSDERMAL PATCH COMPRISING THE SAME

(71) Applicant: Tsung-Min Hsu, Taipei (TW)

(72) Inventor: Tsung-Min Hsu, Taipei (TW)

( * ) Notice: Subject to any disclaimer, the term of this patent is extended or adjusted under 35 U.S.C. 154(b) by 0 days.

(21) Appl. No.: 15/842,117

(22) Filed: Dec. 14, 2017

(65) Prior Publication Data
US 2019/0185421 A1 Jun. 20, 2019

(51) Int. Cl.
| | |
|---|---|
| *A61K 9/70* | (2006.01) |
| *A61P 25/28* | (2006.01) |
| *A61K 31/27* | (2006.01) |
| *A61K 9/00* | (2006.01) |
| *A61K 47/02* | (2006.01) |
| *A61K 47/12* | (2006.01) |
| *A61K 47/32* | (2006.01) |
| *C07C 269/08* | (2006.01) |
| *C07C 271/44* | (2006.01) |

(52) U.S. Cl.
CPC .......... *C07C 269/08* (2013.01); *A61K 9/0014* (2013.01); *A61K 9/7053* (2013.01); *A61K 9/7084* (2013.01); *A61K 31/27* (2013.01); *A61K 47/02* (2013.01); *A61K 47/12* (2013.01); *A61K 47/32* (2013.01); *A61P 25/28* (2018.01); *C07C 271/44* (2013.01)

(58) Field of Classification Search
CPC .... A61K 31/27; A61K 9/7023; A61K 9/7084; A61P 25/28; C07C 269/08; C07C 271/44
See application file for complete search history.

(56) References Cited

U.S. PATENT DOCUMENTS

| | | | |
|---|---|---|---|
| 2007/0225379 A1* | 9/2007 | Carrara | A61K 9/006 514/756 |
| 2014/0221942 A1* | 8/2014 | Scasso | A61K 47/02 604/307 |

FOREIGN PATENT DOCUMENTS

JP 2017001992 A * 1/2017 ............. A61K 31/27

OTHER PUBLICATIONS

English machine translation of JP 2017001992 A (Tominaga et al.) made Mar. 4, 2019. (Year: 2019).*
Wen-Ching Hao, Studies on Rivastigmine Transdermal Patchs, May 2016, graduate thesis from Chongqing Medical University, China.

* cited by examiner

*Primary Examiner* — Michael B. Pallay
(74) *Attorney, Agent, or Firm* — Sinorica, LLC

(57) ABSTRACT

The present invention provides a method for producing an active ingredient for a rivastigmine free base transdermal patch having preparing a rivastigmine free base; and adding an acidic substance to the rivastigmine free base and subjecting the acidic substance and the rivastigmine free base to a mixed reaction to form a mixture having a pH value from 6.0 to 8.5 as the active ingredient; and a rivastigmine free base transdermal patch having a drug layer comprising the active ingredient. The rivastigmine free base transdermal patch has a stable transdermal transmission time equal to or longer than 48 hours and equal to or less than 168 hours. The active ingredient produced by the method and the transdermal patch having the active ingredient allow effective and smooth release of rivastigmine free base and prolongs the release time to meet the clinical application needs.

1 Claim, 1 Drawing Sheet

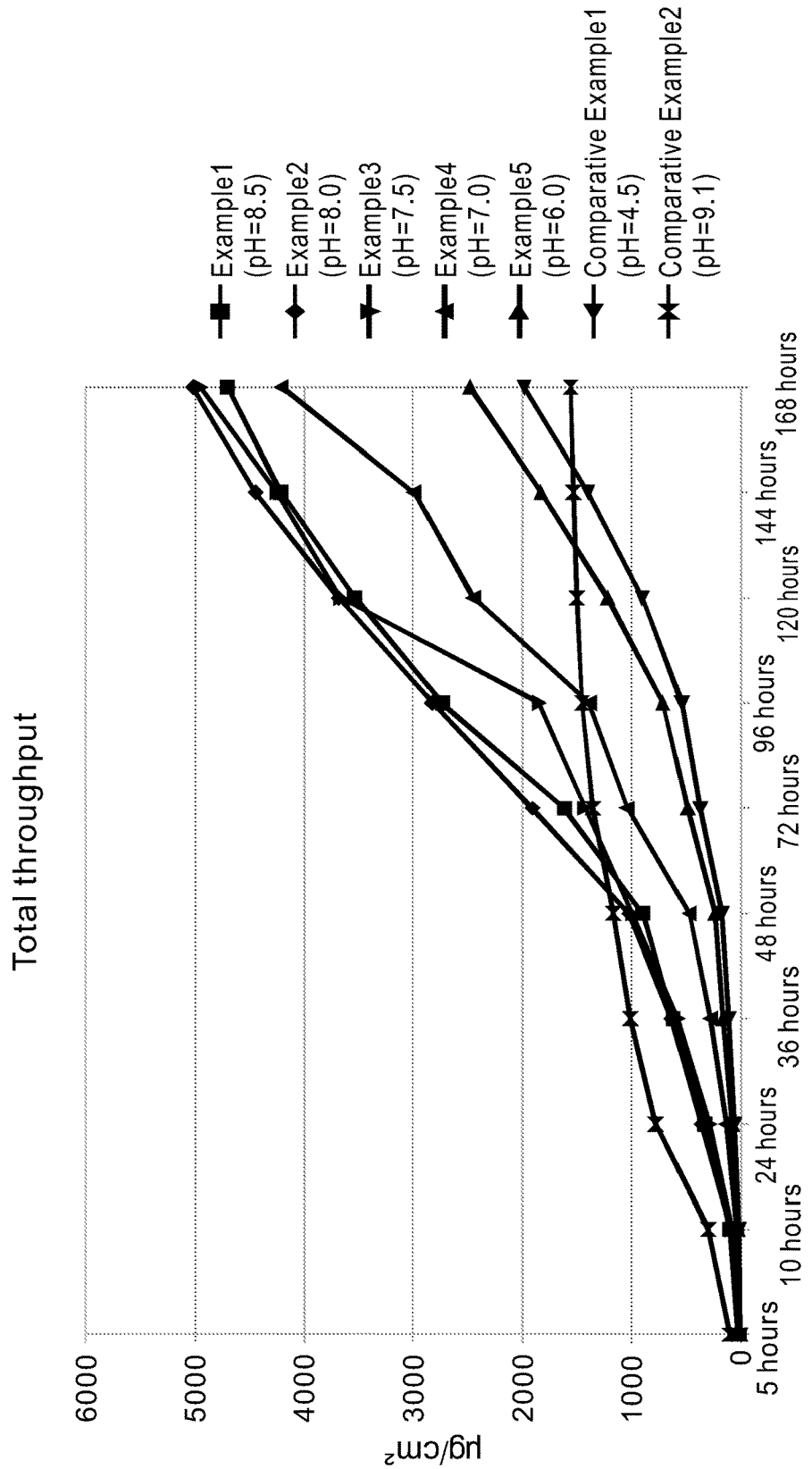

METHOD FOR PRODUCING ACTIVE INGREDIENT FOR RIVASTIGMINE FREE BASE TRANSDERMAL PATCH AND RIVASTIGMINE FREE BASE TRANSDERMAL PATCH COMPRISING THE SAME

BACKGROUND OF THE INVENTION

1. Field of the Invention

The present invention relates to a method for producing an active ingredient for a rivastigmine free base transdermal patch and a rivastigmine free base transdermal patch comprising the active ingredient, especially to a method for producing a long-term sustained releasing ingredient for a rivastigmine free base transdermal patch and a long-term sustained releasing rivastigmine free base transdermal patch comprising the active ingredient.

2. Description of the Prior Art

Rivastigmine is used for dementia caused by, for example, Alzheimer's disease or Parkinson's disease. Conventional rivastigmine pharmaceutical formulations include oral dosage forms and transdermal patch formulations. Because of the expensiveness of rivastigmine, when administered as an oral dosage form, it will result in a decrease in efficacy due to the first pass effect, which in turn leads to a negative effect on cost-effectiveness.

From transdermal patches patients absorb Rivastigmine through the skin instead of through the gastrointestinal tract, which not only avoids the first crossing effect, but also prevents the adverse effects of rivastigmine on the gastrointestinal tract. Therefore, in comparison to oral dosage forms, transdermal patch formulations provide better economic benefits and dosing effect.

Rivastigmine tartrate and rivastigmine free base are effective in the treatment of dementia with rivastigmine. Among them, rivastigmine free base is known for its extremely high transdermal efficiency. However, the short releasing duration of rivastigmine free base fails to sustain slow transdermal release of rivastigmine for more than 36 hours.

Commercially available rivastigmine transdermal patches on market for clinical application employ rivastigmine free base as an active ingredient. However, when administered to patients via the foregoing conventional rivastigmine transdermal patches, the rivastigmine free base as the active ingredient fails to sustain slow transdermal release of rivastigmine for more than 36 hours, thus limits the likelihood of achieving an ideal therapeutic effect. It can also be understood that in the clinical aspect there is an unmet medical need for long-term sustained releasing rivastigmine transdermal patches that promote the therapeutic effects.

SUMMARY OF THE INVENTION

The main objective of the invention is to provide a method for producing an active ingredient for a rivastigmine free base transdermal patch. The method for producing an active ingredient for a rivastigmine free base transdermal patch in accordance with the present invention has excellent transdermal transmission efficiency and is suitable for long-term sustained release of rivastigmine. In order to achieve the foregoing inventive effects, the method in accordance with the present invention comprises: preparing a rivastigmine free base; and adding an acidic substance to the rivastigmine free base to form a mixture having a pH value from 6.0 to 8.5 as the active ingredient for the rivastigmine free base transdermal patch.

Preferably, the pH value of the mixture is from 7.5 to 8.5.

Preferably, the acidic substance is an organic acid selected from the group consisting of carboxylic acid and sulfonic acid.

Preferably, the acidic substance is an organic acid of divalent organic carboxylic acids. For example, the acidic substance may be succinic acid, glutaric acid, adipic acid, methylmalonic acid, carbonic acid, tartaric acid, oxalic acid, or malonic acid.

Preferably, the acidic substance is an inorganic acid.

In another aspect, the present invention provides a rivastigmine free base transdermal patch. The rivastigmine free base transdermal patch in accordance with the present invention comprises a drug layer comprising the active ingredient produced by the foresaid method for a rivastigmine free base transdermal patch, wherein the rivastigmine free base transdermal patch has a stable transdermal transmission time equal to or longer than 48 hours and equal to or less than 168 hours.

Preferably, the drug layer comprises an antioxidant selected from the group consisting of vitamin E, vitamin C, propyl gallate, guaijuan resin, and combinations thereof.

Preferably, the rivastigmine free base transdermal patch further comprises a protective layer and a release film, wherein the drug layer is sandwiched between the protective layer and the release film.

More preferably, the rivastigmine free base transdermal patch further comprises a pharmaceutically controlled release layer sandwiched between the drug layer and the release film and comprising a pressure-sensitive rubber, wherein the pressure-sensitive rubber is made of a synthetic rubber selected from the group consisting of butadiene rubber, styrene-butadiene rubber, chloroprene rubber, nitrile rubber, isoprene rubber, brominated butyl rubber, polyisoprene rubber, silicone rubber, and polyisobutylene rubber.

More preferably, the pharmaceutically controlled release layer comprises an antioxidant, a polyvinylpyrrolidone and 1 wt % to 20 wt % of the active ingredient produced by the foresaid method for a rivastigmine free base transdermal patch.

According to the method for producing the active ingredient of a rivastigmine free base transdermal patch, the rivastigmine free base is mixed with the acidic substance to a specific pH value. The acidic substance is used to adjust the strong positive charge of rivastigmine free base in order to produce a new active ingredient for a rivastigmine free base transdermal patch. When applied to a rivastigmine free base transdermal patch, the active ingredient makes possible the effective and smooth release of rivastigmine free base and prolongs the release time, which solves the problem of the conventional rivastigmine free base transdermal patches that transdermal transmission be largely reduced or blocked. Regarding conventional rivastigmine tartrate transdermal patches, the present invention also provides solution to the failed transdermal transmission efficiency as well as the limited therapeutic effect of the conventional rivastigmine tartrate transdermal patches originated therefrom. Therefore, it is evident that the present invention provides a method for producing the active ingredient for a rivastigmine free base transdermal patch and the rivastigmine free base transdermal patch to meet the clinical application needs.

BRIEF DESCRIPTION OF THE DRAWINGS

FIG. 1 is a graph showing the total throughputs of the rivastigmine free base transdermal patches of Examples 1 to

DETAILED DESCRIPTION OF THE PREFERRED EMBODIMENTS

Example 1

The instant example is directed to the preparation of an active ingredient for a rivastigmine free base transdermal patch and the preparation of the rivastigmine free base transdermal patch using the active ingredient.

In this example, when preparing a rivastigmine free base, 1.9 g of rivastigmine free base was added and thoroughly mixed into a solution made by dissolving 0.36 g of tartaric acid in 0.39 g of pure water to form a mixture being the active ingredient for a rivastigmine free base transdermal patch. The pH value of the mixture, as measured, was 8.5.

The instant example also relates to the preparation of a rivastigmine free base transdermal patch by adding and thoroughly mixing 0.02 g of vitamin E into the above-mentioned mixture of rivastigmine free base and tartaric acid, and by further adding a polyisobutylene rubber as an adhesive in to the rivastigmine free base and tartaric acid mixture with vitamin E. The polyisobutylene rubber contained 8.0 g of polyisobutylene, 2.0 g of C5 resin, and 0.3 g of mineral oil which were dissolved and thoroughly mixed in 15.5 g of n-hexane. 0.75 g of betaine and 1.5 g of cross-linked polyvinylpyrrolidone were then further added and thoroughly mixed into the mixture. The resulting mixture made as above-described were then coated on a release film to form a gel having a thickness from 5 mm to 6 mm and heated in a 65° C. oven for 1 hour to form a drug layer. A protective layer was covered on one side of the drug layer opposite to the release film, that is, the drug layer was sandwiched between the protective layer and the release film to form a three-layer patch comprising the protective layer, the drug layer, and the release film.

Example 2

The instant example is directed to the preparation of an active ingredient for a rivastigmine free base transdermal patch and the preparation of the rivastigmine free base transdermal patch using the active ingredient.

This example is similar to that of the foregoing Example 1 except that in the instant example 1.9 g of rivastigmine free base was added and thoroughly mixed into a solution made by dissolving 0.43 g of tartaric acid in 0.47 g of pure water to form a mixture being the active ingredient for a rivastigmine free base transdermal patch. The pH value of the mixture, as measured, was 8.0.

Example 3

The instant example is directed to the preparation of an active ingredient for a rivastigmine free base transdermal patch and the preparation of the rivastigmine free base transdermal patch using the active ingredient.

This example is similar to that of the foregoing Example 1 except that in the instant example 1.9 g of rivastigmine free base was added and thoroughly mixed into a solution made by dissolving 0.5 g of tartaric acid in 0.55 g of pure water to form a mixture being the active ingredient for a rivastigmine free base transdermal patch. The pH value of the mixture, as measured, was 7.5.

Example 4

The instant example is directed to the preparation of an active ingredient for a rivastigmine free base transdermal patch and the preparation of the rivastigmine free base transdermal patch using the active ingredient.

This example is similar to that of the foregoing Example 1 except that in the instant example 1.9 g of rivastigmine free base was added and thoroughly mixed into a solution made by dissolving 0.55 g of tartaric acid in 0.6 g of pure water to form a mixture being the active ingredient for a rivastigmine free base transdermal patch. The pH value of the mixture, as measured, was 7.0.

Example 5

The instant example is directed to the preparation of an active ingredient for a rivastigmine free base transdermal patch and the preparation of the rivastigmine free base transdermal patch using the active ingredient.

This example is similar to that of the foregoing Example 1 except that in the instant example 1.9 g of rivastigmine free base was added and thoroughly mixed into a solution made by dissolving 0.65 g of tartaric acid in 0.7 g of pure water to form a mixture being the active ingredient for a rivastigmine free base transdermal patch. The pH value of the mixture, as measured, was 6.0.

Comparative Example 1

The instant comparative example is directed to the preparation of an active ingredient for a rivastigmine free base transdermal patch and the preparation of the rivastigmine free base transdermal patch using the active ingredient.

This comparative example is for comparison with the foregoing Examples 1 to 5 and is similar to that of the foregoing Example 1 except that in the instant comparative example 1.9 g of rivastigmine free base was added and thoroughly mixed into a solution made by dissolving 1.1 g of tartaric acid in 1.2 g of pure water to form a mixture being the active ingredient for a rivastigmine free base transdermal patch. The pH value of the mixture, as measured, was 4.5.

Comparative Example 2

The instant comparative example is directed to preparation of a rivastigmine free base transdermal patch directly using a rivastigmine free base as an active ingredient.

In this comparative example, 1.9 g of rivastigmine free base was prepared, pH value of which, as measured, were 9.10. This 1.9 g of rivastigmine free base was thoroughly mixed with 0.02 g of vitamin E, and further with a polyisobutylene rubber as an adhesive. The polyisobutylene rubber contained 8.0 g of polyisobutylene, 2.0 g of C5 resin, and 0.3 g of mineral oil which were dissolved and thoroughly mixed in 15.5 g of n-hexane. 0.75 g of betaine and 1.5 g of cross-linked polyvinylpyrrolidone were then further added and thoroughly mixed to form a mixture. The mixture made as above-described were then coated on a release film to form a gel having a thickness from 5 mm to 6 mm and heated in a 65° C. oven for 1 hour to form a drug layer. A protective layer was covered on one side of the drug layer opposite to the release film, that is, the drug layer was sandwiched between the protective layer and the release film to form a three-layer patch comprising the protective layer, the drug layer, and the release film.

Test Example 1

The instant test example is for comparing the transdermal transmission throughputs of rivastigmine free base transdermal patches comprising drug layers employing respectively the active ingredients made in the previously described Examples 1 to 5 and Comparative Examples 1 and 2. The testing method applied in the instant test example was to test the foresaid rivastigmine free base transdermal patches employing respectively the active ingredients made in Examples 1 to 5 and Comparative Examples 1 and 2 using Bama pig skin. Each of the rivastigmine free base transdermal patches were cut into a disk with a diameter of 1.2 cm, attached to a surface of the stratum corneum of a sheet of Bama pig skin cut into a disk with a diameter of 1.5 cm, and clamped with which between a diffusing chamber and a receptor chamber of a transdermal transmission diffusion instrument. The stratum corneum of the skin faces upward. A receptor solution was injected into the receptor chamber. The receptor solution was a phosphate buffer (pH=7.4). Receptor solutions were respectively sampled in corresponding time points and measured with a high performance liquid phase method.

The throughput data of the aforementioned rivastigmine free base transdermal patches are summarized in Table 1 below.

TABLE 1

| The total throughputs by time of rivastigmine free base transdermal patches | | | | | | | |
|---|---|---|---|---|---|---|---|
| Total throughput ($\mu g/cm^2$) | Example 1 (pH = 8.5) | Example 2 (pH = 8.0) | Example 3 (pH = 7.5) | Example 4 (pH = 7.0) | Example 5 (pH = 6.0) | Comparative Example1 (pH = 4.5) | Comparative Example2 (pH = 9.1) |
| 5 hours | 25 | 31 | 15 | 12 | 9 | 2 | 101 |
| 10 hours | 101 | 96 | 80 | 41 | 27 | 13 | 299 |
| 24 hours | 332 | 366 | 292 | 137 | 80 | 59 | 777 |
| 36 hours | 618 | 632 | 584 | 278 | 165 | 111 | 1012 |
| 48 hours | 896 | 1024 | 995 | 472 | 237 | 178 | 1163 |
| 72 hours | 1618 | 1912 | 1424 | 1037 | 491 | 374 | 1357 |
| 96 hours | 2736 | 2823 | 1851 | 1390 | 713 | 539 | 1454 |
| 120 hours | 3535 | 3684 | 3667 | 2452 | 1218 | 901 | 1503 |
| 144 hours | 4214 | 4450 | 4250 | 2991 | 1830 | 1401 | 1535 |
| 168 hours | 4704 | 5023 | 4952 | 4210 | 2483 | 1986 | 1558 |

With reference to FIG. 1, according to the trend of the data in Table 1 presented in the line chart shown in FIG. 1, the total throughput of the rivastigmine free base transdermal patch of Comparative Example 1 until 168 hours as the end point of the measurement was inferior to those of Examples 1 to 4. Comparing Example 5 and Comparative Example 1, it was also evident that Comparative Example 1 presented a total throughput of the rivastigmine free base transdermal patch of Comparative Example 1 until 72 hours was of lesser quantity than that of Example 5. In accordance with the tendency of Example 5 shown in FIG. 1, it was also reasonably expected that the total throughput of the rivastigmine free base transdermal patch of Comparative Example 1 until 168 hours as the end point of the measurement would be inferior to that of Example 5.

The observation of Comparative Example 2, which directly use rivastigmine free base as the active ingredient of a rivastigmine free base transdermal patch, indicates that it provided desired transdermal transmission efficiency only at the beginning stage. However, in the follow-up long-term sustained releasing effect, it demonstrated that the release of the drug significantly reduced, which was completely disproportionate compared with the high throughput transmission in the previous stage. It should be noted that even if Comparative Example 2 exhibited a good transdermal transmission throughput at the beginning stage of the administration, the total throughput in long-term sustained release was the lowest among Examples 1 to 4 and Comparative Examples 1 and 2. Taking the long term tendency of Example 5 shown in FIG. 1, it was also reasonably expected that the total throughput of the rivastigmine free base transdermal patch of Comparative Example 2 would be lower than that of Example 5. It is therefore evident that Comparative Example 2 does depict the problem and shortcomings of conventional rivastigmine free base transdermal patches.

Each of the active ingredients of the rivastigmine free base transdermal patches of Examples 1 to 5 has been treated with an appropriate amount of an acidic substance for adjusting its pH value from 6.0 to 8.5. When rivastigmine is administered with the rivastigmine free base transdermal patches of Examples 1 to 5, these patches accommodate well on the skin of patients where large amount of charge resident. The active ingredients of the rivastigmine free base transdermal patches of Examples 1 to 5, each of which has been treated with the acidic substance, come with appropriately reduced positive charge. Thus the transdermal transmissions of the foregoing patches are free from the restrains and limitations originated from the positively charged functional groups of untreated rivastigmine free base. Rather, the transdermal transmissions are performed with active ingredients or the acidic substance treated rivastigmine free bases in a smooth and effective manner to steadily release rivastigmine so as to enable an ideal therapeutic effect.

In Comparative Example 1, the active ingredient was a rivastigmine free base treated a large amount of acidic substance, that is, 0.64 g of tartaric acid dissolved in 0.7 g of pure water, therefore the rivastigmine free base was deprived of too much positive charge, which resulted into insufficient tensile force and failure to facilitate transdermal transmission of rivastigmine molecules. As shown with actual values, the total throughput of Comparative Example 1 was superior merely to Comparative Example 2 with the untreated rivastigmine free base. Difference was huge between Comparative Example 1 and Examples 1 to 5. It is therefore known that Comparative Example 1 failed to provide the inventive effects of the present invention.

In view of the above, the present invention provides a method for producing an active ingredient for a rivastigmine free base transdermal patch, by mixing rivastigmine free base with an acidic substance to specific pH value range, and using the acidic substance to regulate the excessively strong positive charge of rivastigmine free base, so as to produce a new active ingredient for rivastigmine free base transdermal patches. As a feature of the present invention, the acidic substance include but are not limited to the tartaric acid used in the above-described Examples 1 to 5, such as various organic acids or inorganic acids which can be used to adjust the positive charge to reduce the excessively high transdermal transport tension, which are for example: carboxylic acids, sulfonic acids, divalent organic carboxylic acids, succinic acid, glutaric acid, adipic acid, methylmalonic acid, carbonic acid, tartaric acid, oxalic acid, and malonic acid. Application of the active ingredients of the present invention in rivastigmine free base transdermal patches prolongs effective and smooth release of rivastigmine free base, which improves the releasing duration of untreated rivastigmine free base and in turn solves problems in lack of ideal therapeutic effect due to reduction or blocking of transdermal transmission thereof. Therefore, the present invention is capable of providing a method for producing the active ingredient for a rivastigmine free base transdermal patch and a rivastigmine free base transdermal patch to meet the clinical needs.

In addition, a rivastigmine free base transdermal patch to which the active ingredient of the present invention may be applied may be a four-layer transdermal patch further comprising a pharmaceutically controlled release layer. The pharmaceutically controlled release layer is preferably sandwiched between the drug layer and the release film and comprises a pressure-sensitive rubber, so as to provide convenient adhesion for easier administration to the skin of a patient. The foregoing pressure-sensitive rubber is pharmaceutically compatible to the application of rivastigmine with specific limitations. The pressure-sensitive rubber may be, for example, made of a synthetic rubber being butadiene rubber, styrene-butadiene rubber, chloroprene rubber, nitrile rubber, isoprene rubber, brominated butyl rubber, polyisoprene rubber, silicone rubber, or polyisobutylene rubber. When producing the rivastigmine free base transdermal patch, the patch may be made that the drug layer or the pharmaceutically controlled release layer further has an antioxidant, which includes a variety of antioxidants pharmaceutically compatible to rivastigmine. The antioxidant may be, for example, vitamin E, vitamin C, propyl gallate, and guaijian resin. The drug layer or the pharmaceutically controlled release layer may comprise only one specific antioxidant or a combination of antioxidants. Furthermore, the pharmaceutically controlled release layer may include the active ingredient in accordance with the present invention to an amount of equal or less than 20 wt % of the pharmaceutically controlled release layer so that the rivastigmine free base transdermal patch may additionally provide buffering effect to further smooth the steady release of the active ingredient.

In addition, the above-mentioned active ingredient may be further added to the aforementioned drug-controlled release layer in an amount equal to or less than 20 wt %, preferably 1 wt % to 20 wt %, to further provide a cushioning functionality, so that the release of the drug effect is more moderate and stable.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for producing a rivastigmine free base transdermal patch, comprising:
   preparing a rivastigmine free base;
   adding an acidic substance to the rivastigmine free base to form an aqueous mixture having a pH value from 7.5 to 8.5 as an active ingredient for the rivastigmine free base transdermal patch, wherein the acidic substance is tartaric acid;
   adding and mixing polyisobutylene rubber, n-hexane and cross-linked polyvinylpyrrolidone into the aqueous mixture to form a resulting mixture; and
   heating the resulting mixture to form a drug layer of the rivastigmine free base transdermal patch.

* * * * *